United States Patent [19]

Mina

[11] Patent Number: 5,059,908
[45] Date of Patent: Oct. 22, 1991

[54] AMPERIMETRIC MEASUREMENT WITH CELL ELECTRODE DEPLATING

[75] Inventor: Charles J. Mina, Willow Grove, Pa.

[73] Assignee: Capital Controls Company, Inc., Colmar, Pa.

[21] Appl. No.: 531,047

[22] Filed: May 31, 1990

[51] Int. Cl.$^5$ .............................. G01N 27/02
[52] U.S. Cl. ............................ 324/444; 204/406; 324/425
[58] Field of Search ............... 324/439, 444, 425, 438, 324/678, 447; 204/153.1, 153.17, 400, 406, 415

[56] References Cited

U.S. PATENT DOCUMENTS

| | | | |
|---|---|---|---|
| 3,341,430 | 9/1967 | Wickerham et al. | 324/425 |
| 3,669,868 | 6/1972 | Lieber et al. | 204/228 |
| 3,912,613 | 10/1975 | Heuser | 204/406 |
| 3,957,592 | 5/1976 | Young | 204/406 |
| 4,033,830 | 6/1977 | Fletcher, III | 204/1 T |
| 4,042,465 | 8/1977 | Morong, III | 204/406 |
| 4,059,406 | 11/1977 | Fleet | 73/61.1 C |
| 4,072,594 | 2/1978 | Outsuka et al. | 204/406 |
| 4,077,861 | 3/1978 | Lauer | 204/1 T |
| 4,123,700 | 10/1978 | LaConti et al. | 324/182 |
| 4,189,367 | 2/1980 | Connery et al. | 204/406 |
| 4,211,615 | 7/1980 | Hallberg et al. | 204/1 T |
| 4,227,988 | 10/1980 | Galwey | 204/406 |
| 4,230,554 | 10/1980 | Blanke | 204/406 |
| 4,244,800 | 1/1981 | Frazzini et al. | 204/1 T |
| 4,269,684 | 5/1981 | Zick | 204/406 |
| 4,301,413 | 11/1981 | De Steur | 324/438 |
| 4,416,736 | 11/1983 | Huber | 204/1 T |
| 4,459,180 | 7/1984 | Fogel | 204/1 T |
| 4,496,433 | 1/1985 | Annino et al. | 204/1 T |
| 4,496,454 | 1/1985 | Berger | 204/402 |
| 4,595,462 | 6/1986 | Vangaever et al. | |
| 4,705,617 | 11/1987 | Beebe et al. | 204/402 |
| 4,729,824 | 3/1988 | Giner | 204/415 |
| 4,730,479 | 3/1988 | Pyke et al. | 73/23 |
| 4,808,930 | 2/1989 | Kaiser | 324/442 |
| 4,950,378 | 8/1990 | Nagata | 204/406 |

Primary Examiner—Kenneth A. Wieder
Assistant Examiner—Maura K. Regan
Attorney, Agent, or Firm—Howson & Howson

[57] ABSTRACT

In an amperimetric measurement apparatus comprising an amperimetric cell having a pair of electrodes arranged for contact with a solution, a potential difference is established between the electrodes, and a corresponding electric current is conducted in a forward direction through a current path which includes the electrodes and the solution. An output corresponding to the current indicates the concentration of a solute in the solution. The electrical charge passing through said cell in response to said potential difference is monitored by an integrator. The forward current is interrupted repeatedly and a reverse electric current is imposed on the cell during the interruptions of forward current. The magnitude and duration of the reverse current are regulated in response to the electrical charge flow corresponding to the forward current, so that the net flow of charge through the cell over a time period including an equal number of intervals of forward and reverse current intervals is substantially zero. Consequently, ionic contaminants, which tend to be plated onto cell electrodes as a result of the forward current are removed substantially completely by deplating, without the risk of producing inaccurate measurements by placing the cell in a reverse charging condition.

16 Claims, 2 Drawing Sheets

AMPERIMETRIC MEASUREMENT WITH CELL ELECTRODE DEPLATING

BRIEF SUMMARY OF THE INVENTION

This invention relates to apparatus and methods for amperimetric measurement of the gas content of a liquid, and more particularly to an amperimetric measurement apparatus having improved means for deplating contaminants which have been plated out onto electrode surfaces in the amperimetric cell during measurement.

An amperimetric cell is a device in which chemical analysis is carried out by the measurement of the magnitude of an electric current between a pair of electrodes. Although an amperimetric cell has a variety of uses, it is particularly useful for the quantitative measurement of dissolved gases. The amount of gas dissolved in a liquid affects the electrical equivalent or effective resistance of the solution. Consequently, it is possible to determine the quantity of dissolved gas by amperimetric measurement.

A major problem encountered in amperimetric measurement of dissolved gases is that, in many cases, the gas solution is contaminated by metallic ions or dissolved minerals. These contaminants eventually plate out onto the electrodes of the cell and change the electrical characteristics of the electrodes by changing the effective electrochemical potential of the electrode material. One result of the plating of contaminants onto the electrodes is that the measured cell current is altered in an unpredictable manner, and erroneous readings are produced. The building up of contaminants on the cell electrodes also causes a continuous drift in the output signal of the cell, thereby impairing the accuracy of the measurement.

One approach to the above problem is to use membrane cells, i.e. cells in which a semi-permeable membrane is used to prevent plating of contaminants onto the cell electrodes. The membrane is effective in preventing plating, but it reduces the sensitivity and accuracy of the cell and also requires a longer time for carrying out a measurement. Membrane cells also become depleted over a period of time and require frequent replacement. They are also physically delicate, and the membranes are easily punctured.

Another problem encountered in amperimetric measurement is electrode polarization. Costly noble metals, for example silver, gold or platinum, are used as electrode materials to avoid polarization effects. However, as a practical matter, because of the high cost of noble metals, the electrodes must be made small in size. Consequently, the cell is capable of producing only a small signal. Another problem with noble metal electrodes is that, although they do not polarize, they are susceptible to plating by ionic contaminants, in the same manner as are electrodes made of less expensive materials. The effect of plating of contaminants is more pronounced in the case of small noble metal electrodes than in the case of larger electrodes.

Another approach to the avoidance of the problems caused by contaminants in amperimetric measurement is the use of mechanical abrasion. Mechanical abrasion is used to depolarize cell electrodes by removing products of electrochemical reactions such as soft oxides, and to remove biological fouling, mechanical fouling and oil films. Mechanical abrasion is not particularly effective in removing plated ionic contaminants.

One way in which the problems caused by plating of ionic contaminants have been addressed is to apply a reverse current to the measurement electrodes in order to cause deplating to take place. Typically the reverse current is applied over a long period of time. Deplating interrupts the measurement. Therefore, there are long intervals during which the electrodes cannot produce a signal indicative of the measured variable. To produce effective deplating, it has been considered necessary to apply a reverse current in excess of what is actually needed, since the exact amount of current needed is unknown. The excess current places the cell in a reverse charging condition, causing the normal operation to be unreliable initially, until the electrodes stabilize to a steady state condition. Depending on the choice of electrode materials, the application of an excessive reverse current may cause the material of one electrode to be plated onto the other electrode, eventually ruining the cell.

Heretofore, in deplating by the application of reverse current, the amount of reverse current and the duration of its application have been determined empirically. These parameters vary depending on many factors, and consequently a high level of operator skill is required to achieve effective deplating of cell electrodes without placing the cell in a reverse charging condition.

The principal object of this invention is to achieve greater measurement accuracy and reliability in amperimetric measurement by preventing the build-up of ionic contaminants onto cell electrodes by electroplating. Another object of the invention is the avoidance of excessive deplating current and the elimination of the resulting measurement errors. Still other objects of the invention include one or more of the following: the achievement of highly accurate measurements at low levels of solute concentration; the extension of useful cell life; the improvement of cell output signal integrity; the avoidance of electrode polarization; and the elimination of the need for noble metal electrodes.

The invention addresses the foregoing objects in an amperimetric cell having a pair of electrodes arranged for contact with a solution, in which a potential difference is established between the electrodes, a corresponding electric current is conducted in a forward direction through a current path which includes the electrodes and the solution, and an output, corresponding to the forward current, indicates the concentration of a solute in the solution. In accordance with the improvement of the invention, the electrical charge passing through the cell in response to the potential difference is monitored by an integrator. The forward current is interrupted repeatedly, and a reverse electric current is imposed on the cell during the interruptions of forward current. The magnitude and duration of the reverse current are regulated in response to the electrical charge flow corresponding to the forward current, so that the net flow of charge through the cell over a time period including an equal number of intervals of forward and reverse current intervals is substantially zero. Consequently, ionic contaminants, which tend to be plated onto cell electrodes as a result of the forward current are removed substantially completely by deplating, without the risk of producing inaccurate measurements by placing the cell in a reverse charging condition.

Further objects and advantages of the invention will be apparent from the following description, when read in conjunction with the drawings.

DETAILED DESCRIPTION

Figure 1:
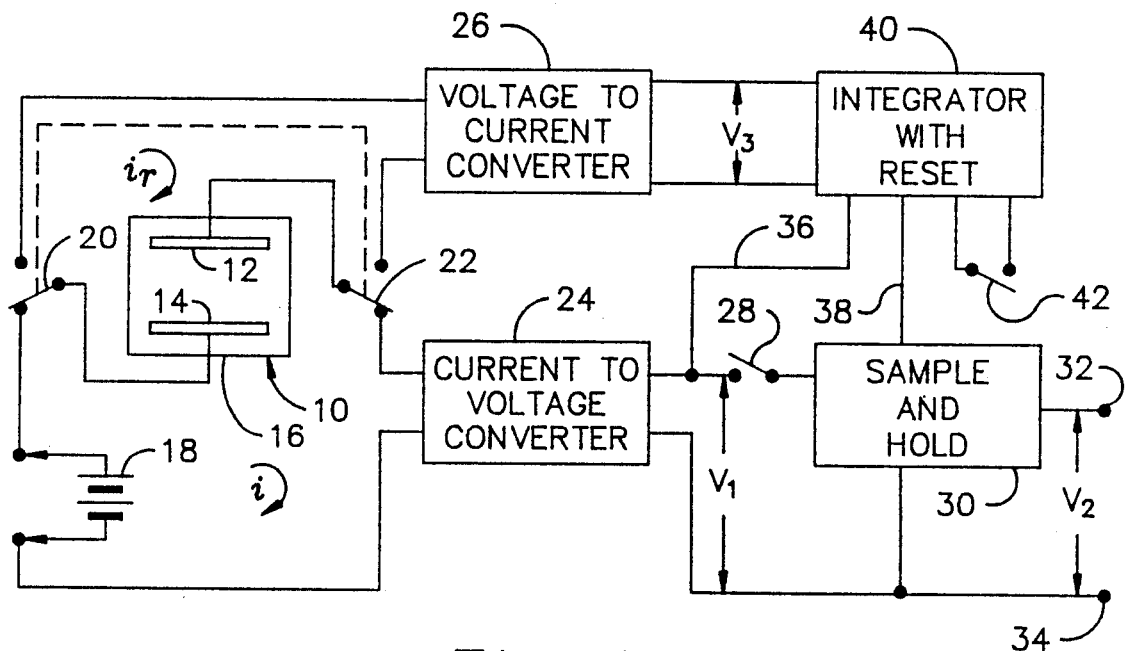
FIG. 1 is a schematic diagram showing an amperimetric cell with an electrode purging circuit in accordance with the invention.

The apparatus shown in FIG. 1 comprises a conventional amperimetric cell 10 including a pair of electrodes 12 and 14 and a container 16 for holding a liquid in contact with the electrodes. The cell 10 is typically, but not necessarily, of the flow-through type for carrying out measurements on a continuously flowing liquid.

The amperimetric cell 10 may have electrodes of dissimilar materials, in which case a natural electrochemical potential exists between the electrodes. This natural potential may itself be the sole source of the potential difference between the electrodes. Alternatively a bias voltage may be added or subtracted from the natural electrochemical potential. In FIG. 1, a battery 18 is shown for applying a bias voltage. The bias voltage can, of course, be supplied by a conventional regulated D.C. power supply instead of by a battery.

Alternatively, the amperimetric cell may have electrodes of identical material. If the electrodes are of identical material, a bias voltage is always applied.

Figure 2:
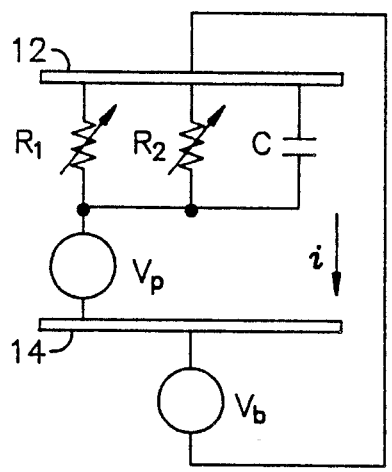
FIG. 2 is a schematic diagram showing an electrical model of an amperimetric cell having electrodes of dissimilar materials.

In the case of a cell having electrodes of dissimilar materials, the electrical model, as shown in FIG. 2 includes a resistance $R_1$, representing the effective resistance of the cell due to electrolytic conductivity and other interfering agents, a resistance $R_2$, representing resistance due to the presence of the dissolved gas to be measured, and a capacitance C, which is inherent in the configuration of the cell. A voltage source $v_p$, represents the electrochemical potential due to the difference between the electrode materials. A voltage source $v_b$ represents the optional bias voltage.

Resistance $R_1$ varies as the electrolytic conductivity of the cell changes, and as the amounts of interfering agents change. $R_1$ also changes with changes in $v_p$ and $v_b$. Resistance $R_2$ varies in accordance with the amount of dissolved gas. $R_2$ also varies with changes in $v_p$ and $v_b$, but in a different manner. In accordance with conventional amperimetric practice, the bias voltage $v_b$ is selected to minimize undesired current through resistance $R_1$ while allowing desired current through resistance $R_2$. The total cell current i is therefore a measure of the concentration of dissolved gas in the liquid in the cell.

Figure 3:
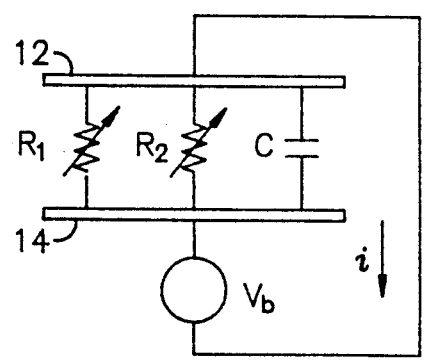
FIG. 3 is a schematic diagram showing an electrical model of an amperimetric cell having electrodes of similar materials.

In the case of a cell having electrodes of similar materials, the electrical model is shown in FIG. 3. If the cell of FIG. 3 is dimensional identical to the cell of FIG. 2, and external bias voltage $v_b$ is chosen to correspond to the sum of voltages $v_p$ and $v_b$ in FIG. 2, then the resulting total cell current i in FIG. 3 corresponds to the total cell current i in FIG. 2.

Returning to FIG. 1, the electrodes 12 and 14 of amperimetric cell 10 are connected respectively to the armatures 20 and 22 of a DPDT switch, shown in a position in which cell current i is conducted from electrode 12, through the input terminals of a current-to-voltage converter 24, and through bias source 18, to electrode 14. While the DPDT switch is shown in mechanical form for ease of illustration, it should be understood that the switch may be composed of transistors or similar electronic switching devices. Whether the DPDT switch is mechanical or electronic, its operation is timed by a timer (not shown) so that cell electrodes 12 and 14 are switched periodically from the position shown to an alternative position in which the forward current i is interrupted, and a reverse current $i_r$ is conducted through the cell from the output terminals of a voltage-to-current converter 26.

Another timer-controlled switch 28 is intermittently closable to connect the voltage output $v_1$ of current-to-voltage converter 24 to a sample and hold module 30, which delivers an output voltage $v_2$ at terminals 32 and 34. Voltage $v_2$ is the output signal corresponding to the measured variable. Voltage $v_2$ can be used to operate a chart recorder or other indicator, or can be recorded by any of a variety of digital or analog recording devices, or connected directly or indirectly to a process control computer.

The voltage output $v_1$ of converter 24 is connected through lines 36 and 38 to an electronic integrator 40, which can be a conventional operational amplifier having a capacitance in a feedback loop, or any of a variety of conventional integrating devices, including programmed microprocessors, for example. A timer-operated resetting switch is shown at 42.

The voltage output $v_3$ of integrator 40 is connected to the input terminals of voltage-to-current-converter 26.

Figure 4:
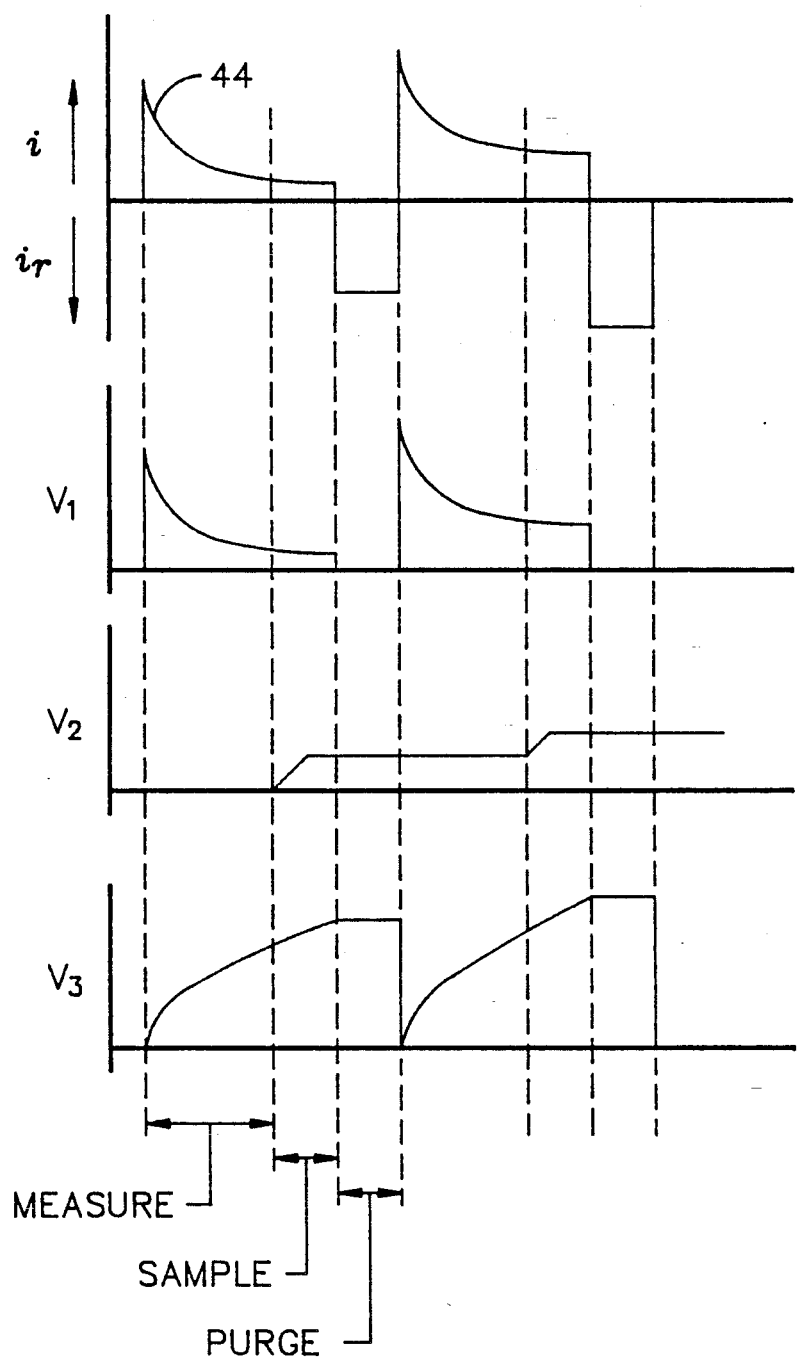
FIG. 4 is a diagram showing the magnitudes of signals at various points in FIG. 1, plotted against time.

The operation of the circuit of FIG. 1 may be best understood by reference to FIG. 4, and takes place as follows.

In each cycle of operation, the circuit of FIG. 1 operates in three successive modes designated "measure", "sample" and "purge". FIG. 4 shows two repetitions of the cycle. As the timer-operated DPDT switch operates to connect armatures 20 and 22 to the loop including the current-to-voltage converter 24 and bias source 18, there is an initial surge of current i at 44. This initial surge of current is believed to be due to the discharging of the internal cell capacitance C (FIGS. 2 and 3). The time required for the surge current to decay is affected by cell resistance $R_1$, as well as by the resistance $R_2$ due to the measured variable. After the initial surge, the current i levels off at 46, and is substantially flat during the "sample" interval. The output $v_1$ of the current to voltage converter follows cell current i during the "measure" and "sample" intervals. At the beginning of the "sample" interval, switch 28 closes, and module 30 takes a sample corresponding to the steady state value of the voltage $v_1$ at the output of converter 24. At the end of the "sample" interval, switch 28 reopens, and sample and hold module 30 retains, at its output terminals 32 and 34, a voltage $v_2$, which corresponds to the level of $v_1$ at the end of the "sample" interval. The sample interval should be long enough to allow the sample and hold module 30 to reproduce, as voltage $v_2$, the voltage $v_1$ at the output of the current-to-voltage converter.

During the "measure" and "sample" intervals, in the meanwhile, integrator 40 produces an output $v_3$, which is proportional to the time integral of the forward cell current i. The integrator output represents the total number of electrons which have reacted in the cell from the onset of the "measure" interval. At the end of the "sample" interval, the switch armatures 20 and 22 shift so that the cell 10 is connected to the output of voltage-to-current converter 26. The current delivered by the output of the voltage-to-current converter corresponds the voltage $v_3$ at the output of the integrator. During the "purge" interval following the end of the "sample" interval, voltage $v_3$ is held at a constant value representing the total charge q which passed through the cell during the immediately preceding "measure" and "sample" intervals. Voltage-to-current converter 26 is calibrated so that, during the fixed "purge" interval, the current level at its output delivers a charge in the reverse direction through the cell which is identical to the charge q resulting from the forward current. This restores the cell to the condition it was in immediately prior to the onset of the "measure" interval. The integrator output is reset to zero at the end of the "purge" interval by momentary timer operation of switch 42. Switch armatures 20 and 22 are also returned to the positions shown in FIG. 1, and another cycle, consisting of "measure", "sample" and "purge" intervals begins. The output of the sample and hold module may rise or fall, depending on the level of concentration of solute in the cell during the "measure" and "sample" intervals.

In the embodiment described, the "purge" interval is held constant, and the reverse current $i_r$ is adjusted. It is of course possible to modify the apparatus to provide for adjustment of the purge interval while keeping the reverse current constant, or to provide for adjustment of both the purge interval and the reverse current.

The amount of reverse current $i_r$ and the duration of the "purge" interval $t_p$ are determined by the following equation:

$$i_r \cdot t_p = -\int_0^{(t_m + t_s)} i\, dt = -q$$

where:
 i is the current flowing in the cell during the "measure" and "sample" intervals;
 q is the charge transferred in the cell during the "measure" and "sample" intervals;
 $t_m$ is the duration of the "measure" interval; and
 $t_s$ is the duration of the "sample" interval.

The invention enables the electrodes of amperimetric cells to remain free of surface degradation, and therefore allows for more stable measurements. The electrodes are maintained in a pristine condition, which significantly improves the accuracy and reliability of measurements.

The invention eliminates the need for membranes in many cases, and consequently provides a way to improve sensitivity, accuracy, useful life, ruggedness and speed of measurement over what is possible with a membrane-type cell.

While the invention does not require the use of membranes, it may be used to enhance the performance of a membrane-type cell by rejuvenating the cell. This is achieved because the circuit of FIG. 1 is capable of reversing the internal electrochemical polarizing reaction which takes place in the cell. Rejuvenation of a membrane-type cell significantly extends its operating life by preventing depletion by polarization. The invention also reduces the characteristically slow response and signal degradation of a membrane cell near the end of its useful life.

Although the invention may be used with noble metal electrodes (using an appropriate biasing voltage), it is primarily intended to work with any selection of electrically conductive electrode material, thereby eliminating the high cost of noble metal electrodes while achieving high sensitivity and accuracy.

The system of the invention can be used in conjunction with mechanical abrasion, where the abrasion is used to effect depolarization by removal of certain products of electrochemical reaction such as soft oxides, and to remove biofouling and other mechanical fouling of electrodes such as oil films. Mechanical abrasion may be used to remove much of the reaction products, thereby making the settings of the electrode purging circuit of the invention less critical.

Numerous modifications can be made to the apparatus described. For example, while the purging circuit can utilize discrete components such as timers, relays and electronic circuit modules, the same results can be accomplished using integrated circuits, solid state timers, and solid state switches. Switch 20 in FIG. 1 can be eliminated in favor of a direct three-way connection, provided complete isolation of the voltage-to-current converter 26 from the current-to-voltage converter 24 is not necessary.

A digital computer can take the place of one or more of the components of FIG. 1. For example, the computer can perform integration digitally, and can control the timing of the various switches, as well as adjustment of the bias voltage on the cell. A digital computer can also eliminate the need for a sample and hold module, and can reduce the sampling time to an insignificantly small interval. A digital computer can also reduce the duration of the "measure" interval by continuously measuring the rate of change of the forward cell current to determine when the steady state has been reached. The time period for the "purge" interval and/or the magnitude of the reverse current can be readily calculated for each cycle by the computer. Since it is desirable to keep the "purge" interval as short as possible, the digital computer can be programmed to maximize the magnitude of the purging current while keeping the "purge" interval as short as possible.

The invention can be applied to electrode systems comprising more than one cell, with purging applied as necessary between those pairs of electrodes which are intended to pass DC current during their normal mode of operation.

Further modifications will be apparent to persons skilled in the art, and may be made without departing from the scope of the invention as defined in the following claims.

I claim:
1. Amperimetric measurement apparatus comprising:
 an amperimetric cell having means for containing a solution, and a pair of electrodes arranged within said cell for contact with said solution;
 means for establishing a forward current through said cell;
 means for repeatedly interrupting said forward current, and, during the interruptions, imposing a reverse current on said cell; and
 control means, including integrator means for integrating the magnitude of the forward current with respect to time, and means responsive to said inte- grator means, for regulating the magnitude and duration of the reverse current so that the net flow of charge through said cell is substantially zero.

2. Amperimetric measurement apparatus according to claim 1 in which the control means includes means for resetting said integrator means during each interruption of said forward current.

3. Amperimetric measurement apparatus according to claim 1 in which the duration of the reverse current during each interruption of the forward current is the same as the duration of the reverse current for every other interruption of the forward current.

4. Amperimetric measurement apparatus according to claim 1 in which the magnitude of the reverse current during each interruption of the forward current is substantially constant.

5. Amperimetric measurement apparatus according to claim 1 including sampling and holding means for taking a sample corresponding to said forward current each time forward current is established through said cell, and for temporarily retaining said sample until the next sample is taken.

6. Amperimetric measurement apparatus according to claim 1 including sampling and holding means for taking a sample corresponding to said forward current each time steady state forward current is established through said cell, and for temporarily retaining said sample until the next sample is taken.

7. Amperimetric measurement apparatus according to claim 1 in which said control means regulates the duration of the forward and reverse current so that the durations of said interruptions are shorter than the durations of the forward current taking place between said interruptions.

8. Amperimetric measurement apparatus comprising:
an amperimetric cell having means for containing a solution, and a pair of electrodes arranged within said cell for contact with said solution;
means for establishing a forward current through said cell;
means for repeatedly interrupting said forward current, and, during the interruptions, imposing a reverse current on said cell; and
control means, responsive to the magnitude and duration of the forward current, for regulating the magnitude and duration of the reverse current so that the net flow of charge through said cell is substantially zero;
in which the control means comprises integrator means for integrating the magnitude of the forward current with respect to time, and current-to-voltage converting means having input terminals in the path of said forward current, and having output terminals connected to said integrating means.

9. Amperimetric measurement apparatus comprising:
an amperimetric cell having means for containing a solution, and a pair of electrodes arranged within said cell for contact with said solution;
means for establishing a forward current through said cell;
means for repeatedly interrupting said forward current, and, during the interruptions, imposing a reverse current on said cell; and
control means, responsive to the magnitude and duration of the forward current, for regulating the magnitude and duration of the reverse current so that the net flow of charge through said cell is substantially zero;
in which said interrupting and reverse current-imposing means comprises a voltage-to-current converter having current output terminals and switching means for connecting the electrodes of said amperimetric cell to said current output terminals during said interruptions.

10. Amperimetric measurement apparatus comprising:
an amperimetric cell having means for containing a solution, and a pair of electrodes arranged within said cell for contact with said solution;
means for establishing a forward current through said cell;
means for repeatedly interrupting said forward current, and, during the interruptions, imposing a reverse current on said cell; and
control means, responsive to the magnitude and duration of the forward current, for regulating the magnitude and duration of the reverse current so that the net flow of charge through said cell is substantially zero;
in which the control means comprises current-to-voltage converting means having input terminals in the path of said forward current and producing an output voltage corresponding to the magnitude of said forward current, and integrator means connected to said current-to-voltage converting means and responsive to said output voltage for producing an output signal corresponding to the time integral of said voltage, and said interrupting and reverse current-imposing means comprises a voltage-to-current converter having an input receiving said output signal of the integrator means and current output terminals delivering a current corresponding to said output signal, and switching means for connecting the electrodes of said amperimetric cell to said current output terminals during said interruptions.

11. Amperimetric measurement apparatus according to claim 10 including sampling and holding means for taking a sample of the output voltage of said current-to-voltage converting means each time forward current is established through said cell, and for temporarily retaining said sample until the next sample is taken.

12. Amperimetric measurement apparatus according to claim 10 including sampling and holding means for taking a sample of the output voltage of said current-to-voltage converting means each time steady state forward current is established through said cell, and for temporarily retaining said sample until the next sample is taken.

13. Amperimetric measurement apparatus comprising:
an amperimetric cell having means for containing a solution, and a pair of electrodes arranged within said cell for contact with said solution;
means for establishing a potential difference between said electrodes and for conducting a forward electric current corresponding to said potential difference in a forward direction through a current path which includes said electrodes and said solution;
means providing an output corresponding to said forward current, said output being an indication of the concentration of a solute in said solution;
means for measuring the electrical charge passing through said cell in response to said potential difference; and means for repeatedly interrupting said current path, and responsive to said measuring means, for imposing a reverse electric current on said cell during the interruptions of forward current, and for regulating the magnitude and duration of the reverse current so that the net flow of charge through said cell over a time period including an equal number of intervals of forward and reverse current intervals is substantially zero;

in which said means for measuring the electrical charge passing through said cell comprises integrating means for integrating the magnitude of said forward current with respect to time during each forward current interval.

14. Amperimetric measurement apparatus according to claim 13 in which said means for interrupting said current path, imposing a reverse electric current on said cell, and regulating the magnitude and duration of the reverse current, regulates the duration of the reverse current so that the durations of said interruptions are shorter than the durations of the forward current taken place between said interruptions.

15. A method of determining the concentration of a solute in a liquid by the use of an amperimetric cell having means for containing a solution, and a pair of electrodes arranged within said cell for contact with said solution, comprising the steps of:

establishing a potential difference between said electrodes, and conducting a forward electric current corresponding to said potential difference in a forward direction through a current path which includes said electrodes and said solution;

providing an output corresponding to said forward current, said output being an indication of the concentration of a solute in said solution;

measuring the electrical charge passing through said cell in response to said potential difference;

repeatedly interrupting said current path, imposing a reverse electric current on said cell during the interruptions of forward current and thereby deplating contaminants plated onto said electrodes during the conduction of forward current through said current path, and regulating the magnitude and duration of the reverse current in response to the measured electrical charge so that the net flow of charge through said cell over a time period including an equal number of intervals of forward and reverse current intervals is substantially zero, whereby substantially complete deplating is effected without placing the cell in a reverse charging condition.

16. The method according to claim 15 in which said reverse current intervals are shorter than said forward current intervals.

* * * * *